(12) United States Patent
Dubois

(10) Patent No.: US 8,808,290 B2
(45) Date of Patent: Aug. 19, 2014

(54) CUSTOMIZED INTRAORAL JAW DISTRACTOR AND USE OF SUCH A DISTRACTOR IN ORDER TO OBTAIN ALMOST CONTINUOUS DISTRACTION

(75) Inventor: Guillaume Dubois, Vanves (FR)

(73) Assignee: OBL, Chatillon (FR)

( * ) Notice: Subject to any disclaimer, the term of this patent is extended or adjusted under 35 U.S.C. 154(b) by 0 days.

(21) Appl. No.: 13/520,404

(22) PCT Filed: Jan. 4, 2011

(86) PCT No.: PCT/FR2011/000004
§ 371 (c)(1),
(2), (4) Date: Jul. 6, 2012

(87) PCT Pub. No.: WO2011/083260
PCT Pub. Date: Jul. 14, 2011

(65) Prior Publication Data
US 2012/0316561 A1   Dec. 13, 2012

(30) Foreign Application Priority Data
Jan. 4, 2010 (FR) .................................... 10 00014

(51) Int. Cl.
*A61B 17/00* (2006.01)
*A61F 4/00* (2006.01)
*A61F 5/04* (2006.01)

(52) U.S. Cl.
USPC ........................................................ 606/58

(58) Field of Classification Search
CPC ............. A61B 17/8071; A61B 17/663; A61B 17/8004
USPC ........ 606/239, 57–58, 282; 623/17.17–17.19; 74/425
See application file for complete search history.

(56) References Cited

U.S. PATENT DOCUMENTS 3,581,592 A * 6/1971 Roehrs et al. ................ 74/424.6

(Continued)

FOREIGN PATENT DOCUMENTS

| EP | 2133033 A1 | 12/2009 |
| FR | 2829684 A1 | 3/2003 |
| JP | 11262491 A | 9/1999 |

OTHER PUBLICATIONS

Nagoya Screw Mfg. Co. Ltd, JP 11262491 A, Sep. 28, 1999, Machine translation performed on Aug. 30, 2013, pp. 1-13.*

(Continued)

*Primary Examiner* — Ellen C Hammond
*Assistant Examiner* — Jacqueline Johanas
(74) *Attorney, Agent, or Firm* — EIP US LLP

(57) ABSTRACT

The invention relates to a customized intraoral jaw distractor, of the type that comprises two anchoring means (1, 2) fastened to the mandibular body at two fixed anchor points, located on either side of the osseous callus. Such a distractor is characterized in that it includes: a) a threaded cylindrical rail (6) connecting the two anchoring means (1, 2); b) a mobile carriage (10) guided to slide on the rail (6) and attached to the osseous segment to be distracted, said mobile carriage being provided with a worm screw (11) with a thread that complements that of the rail and engages with the latter; c) a pin (12) integral to the worm screw (11) and controlling the rotation thereof, said pin, which is parallel to the rail (6), being supported by two bearings (13, 14) arranged on the mobile carriage (10), on either side of the worm screw; d) at least one resilient part (15) through which said pin (12) passes and which rests against one end (16) of the worm screw (11) and against the inner wall (18) of the bearing (14) that faces said end (16). The invention can be used for reconstruction of a missing or deficient osseous segment by means of osteogenic distraction.

20 Claims, 6 Drawing Sheets

(56) References Cited

U.S. PATENT DOCUMENTS

| | | | |
|---|---|---|---|
| 3,900,025 A * | 8/1975 | Barnes, Jr. | 606/71 |
| 4,616,803 A * | 10/1986 | Schils | 251/14 |
| 4,978,348 A * | 12/1990 | Ilizarov | 606/57 |
| 5,364,396 A * | 11/1994 | Robinson et al. | 606/53 |
| 5,372,597 A * | 12/1994 | Hotchkiss et al. | 606/56 |
| 5,435,672 A * | 7/1995 | Hall et al. | 408/68 |
| 5,601,551 A * | 2/1997 | Taylor et al. | 606/54 |
| 5,725,526 A * | 3/1998 | Allard et al. | 606/57 |
| 5,769,850 A * | 6/1998 | Chin | 606/53 |
| 5,834,662 A * | 11/1998 | Stoll et al. | 74/425 |
| 5,902,304 A * | 5/1999 | Walker et al. | 606/71 |
| 6,079,442 A * | 6/2000 | Raymond et al. | 137/554 |
| 6,355,036 B1 * | 3/2002 | Nakajima | 606/57 |
| 6,394,477 B1 * | 5/2002 | Cellini | 280/260 |
| 6,972,020 B1 | 12/2005 | Grayson et al. | |
| 7,182,785 B2 * | 2/2007 | Elsalanty et al. | 623/17.17 |
| 7,703,347 B2 * | 4/2010 | Porinsky et al. | 74/441 |
| 7,998,216 B2 * | 8/2011 | Elsalanty et al. | 623/17.17 |
| 8,177,789 B2 * | 5/2012 | Magill et al. | 606/105 |
| 8,211,106 B2 * | 7/2012 | Labbe et al. | 606/57 |
| 8,287,573 B2 * | 10/2012 | Mulone | 606/282 |
| 2002/0029922 A1 * | 3/2002 | Richardson et al. | 180/444 |
| 2005/0043731 A1 * | 2/2005 | Labbe et al. | 606/57 |
| 2005/0203509 A1 * | 9/2005 | Chinnaian et al. | 606/54 |
| 2005/0203628 A1 * | 9/2005 | Elsalanty et al. | 623/17.17 |
| 2007/0162045 A1 * | 7/2007 | Ahmad | 606/105 |
| 2007/0276502 A1 * | 11/2007 | Elsalanty et al. | 623/17.17 |
| 2009/0088766 A1 * | 4/2009 | Magill et al. | 606/90 |
| 2010/0152734 A1 * | 6/2010 | Mulone | 606/60 |

OTHER PUBLICATIONS

International Search Report for PCT/FR2011/000004 dated Apr. 11, 2011.

* cited by examiner

CUSTOMIZED INTRAORAL JAW DISTRACTOR AND USE OF SUCH A DISTRACTOR IN ORDER TO OBTAIN ALMOST CONTINUOUS DISTRACTION

TECHNICAL FIELD OF THE INVENTION

The present invention concerns a customized intraoral jaw distractor for oral and maxillofacial surgery, with an indication notably in the case of mandibular reconstructions, as well as a very specific use of such a distractor, capable of achieving a distraction in a near continuous mode.

TECHNOLOGICAL BACKGROUND OF THE INVENTION

The replacement of a bone fragment missing in a lower jaw or its repair, for example following a tumor resection or of a severe trauma, or more simply the healing of a bone following an osteotomy performed to modify the bone anatomy, call upon several types of operation techniques.

One of these techniques, distraction osteogenesis, which is a surgical procedure used to reconstruct bone deficiencies or defects or to lengthen the bones of the human body, consists in placing a mechanical apparatus called distractor, whose role is to pull on the osseous callus resulting from the osteotomy in order to elongate it by a distance corresponding to the bone loss.

Whatever the organ concerned, this procedure is performed in several steps that can be broken down in the following manner. First, a surgical procedure is performed, which consists mainly in a sub-periosteal osteotomy in order to fracture the bone to be reconstituted and thus to divide it into at least two segments. After a latency period, these segments are gradually moved apart from one another by means of a distractor. A stabilization phase, in which the bone is allowed to consolidate, obviously precedes the removal of said distractor.

Several distraction osteogenesis techniques have already been successfully used in restoring interrupting substance loss (ISL) in the mandible, in the maxillary or in the malar bone, in particular in the case of ballistic traumas (for example following a firearm suicide attempt) of the face. Distraction osteogenesis enables the bone, gums and surrounding soft tissues to be reconstructed.

Several distractors corresponding to these various techniques for reconstructing loss of bone and of soft tissues of the lower face or middle face are thus already known in the prior art.

Patent application EP0770359, filed by the company Medicon, published on 2 May 1997, describes a mandibular distraction system implementing a first technique. A miniature screw jack, whose two extremities are fastened on each side of the osteogenic callus, exerts a traction on the latter, so as to ensure the new formation of a replacement bone tissue in its place. The whole device is entirely contained in the mouth cavity and the screw can be operated from the outside by a screwdriver type tool.

However, the apparatus remains bulky, notably the telescopic part, and it is impossible to place several of them on the same side of the mandible.

A slightly more compact device, constituted by a miniature double screw jack actuating two symmetric parts, which are integral to anchor points and are guided by two parallel rods, is described in international patent application WO 98/16163 in the name of M. Chin, published on 23 Apr. 1998. The whole apparatus is in a way a rectangle of variable length, whose extension is adjusted by the small jack.

The Chin device is capable of exerting considerable efforts and is particularly adapted for treating the rising branch of the lower jaw (ramus mandibularis), but its mechanical construction is rather complex.

International patent application WO 98/09577 in the name of M. Mommaerts, published on 12 Mar. 1998, pertains to a device still based on the same principle, but in yet another embodiment. The posterior extremity of the telescopic screw system rests directly on an insert placed in the rising branch of the lower jaw (ramus mandibularis), instead of being fastened onto a perforated bar which is common in implantology. The system is thus simpler and more compact, but it enables only the zones of the jaw located far at the rear to be treated.

The advantages of these jaw distractors reside in the fact that their intraoral application is simple and similar to osteosynthesis methods, that they are easy to activate and thus that they are accepted without problems by the patients.

However, a deficiency remains in their therapeutic indications since the prior art as described here above shows that none of these jaw distractors affords continuity in the effort or in the speed of distraction. All these devices operate in a discontinuous fashion, i.e. the bone to be reconstructed is subjected periodically to pulling so as to suddenly be displaced by several tenths of a millimeter each time, wherein the bone's spontaneous ability to regenerate will, in the hours that follow, fill the gap caused by the distractor's traction, and then the distraction operation is performed again by suddenly moving again the bone to be reconstructed by several tenths of a millimeter (according to a reference protocol, accepted by all practitioners, the traction on the bone to be reconstructed is classically performed on a daily or sometimes twice daily basis and this traction is on the order of 0.8 mm to 1 mm per day).

Known distractors furthermore have in most cases one or even two disadvantages: that of being very cumbersome and that of not directly allowing the reconstruction of the bone along a trajectory specific to the treated patient, notably when all or part of this trajectory is curved.

The intraoral jaw distractor according to the invention enables the above mentioned drawbacks to be overcome: the force it applies when striving to move the bone to be reconstructed is near continuous; it is compact, which is of particular importance when considering the intraoral character of such a mechanical device; furthermore, it can be constructed to reflect the patient, it can in a way be specific to each patient, whilst following the rectilinear parts and the curved parts that the bone should ideally follow after its reconstruction.

The geometry of the distractor according to the invention can thus be defined using computers preoperatively, taking into account: the substance loss following the operation or the trauma, the location of this substance loss and the volume of the remaining bone that can be used, and finally the image one wishes to restore in the patient.

GENERAL DESCRIPTION OF THE INVENTION

The present invention thus has as its first object a customized intraoral jaw distractor, designed for the reconstruction by distraction osteogenesis of a missing or deficient osseous segment following a tumor resection, a trauma, a bone deformity or a bone hypoplasia.

In known manner, in that it must cause a bone stimulation through tensile stress, such a distractor comprises two anchoring means attached to the mandibular body at fixed anchor points, located on either side of the osseous callus.

The invention has more precisely as its object an intraoral jaw distractor of this type whose main characteristic is that it includes:

a) a threaded cylindrical rail connecting the two anchoring means, b) a mobile carriage guided to slide on the rail and attached to the osseous segment to be distracted, said mobile carriage being provided with a worm screw with a thread that complements that of the rail and engages with the latter, c) a pin integral to the worm screw and controlling the rotation thereof, said pin, which is roughly parallel to the rail, being supported by two bearings arranged on the mobile carriage, on either side of the worm screw, d) at least one resilient part through which said pin passes and which rests on the one hand against one end of the worm screw and on the other hand against the inner wall of the bearing that faces said end, wherein the distance separating the inner walls of the two bearings of the mobile carriage is equal to the length of the worm screw increased by the height of the resilient part when the latter is resting, i.e. is slack.

The resilient part is ideally either a lock-type washer or a so-called Belleville conical spring washer or a stack of such conical washers arranged in opposition to one another. However, and without this enumeration being limiting in any way, the resilient part can also be any other elastic element such as a spring, a diaphragm or a compressible cylinder, for example made of elastomer.

In order to enable the practitioner or the patients themselves to easily activate the distractor, the pin controlling the rotation of the worm screw is provided with an actuator head lodged in a recess made in the outer wall of the bearing against which the resilient part rests.

Depending on various conceivable embodiments to achieve such an activation, the head provided on the pin controlling the rotation of the worm screw has a slit, or two slits arranged in a cross, or a six-sided blind hole enabling said head to be rotated by means of a screwdriver or an Allen wrench.

In order to ensure perfect fastening and perfect use of the distractor according to the invention, each of its two anchoring means and its mobile carriage are attached in the mandibular body and respectively in the osseous segment to be distracted, by means of at least two attachment points.

Depending on various conceivable embodiments, the means for fastening the mobile carriage in the osseous segment to be distracted have the shape of an I, of a Y or of a crossbuck.

Ideally, in order to enable the mobile carriage to be perfectly guided to slide on the rail, the threaded cylindrical rail of the distractor according to the invention has two diametrically opposed flat faces, wherein the mobile carriage guided to slide on said rail has the form of a cage whose two walls parallel to the longitudinal axis of the rail, joined at their two ends by one and the other of the two bearings supporting the pin of the worm screw, are spaced by a distance very slightly greater than the thickness of said rail taken between its two flat faces. For the same purpose, the threaded cylindrical rail can have a third flat face opposite the bottom of the mobile carriage.

In a first embodiment of the distractor according to the invention, its rail is rectilinear.

In a second embodiment of the distractor according to the invention, its rail forms at least one curve.

In this second case, the different curve or curves of the rail lie in a single plane, which plane is perpendicular to the flat faces of the rail in order to maintain the threading in the vicinity of the neutral fibers of said rail.

Whatever the embodiments of the distractor according to the invention, each of its constitutive elements is advantageously made of a biocompatible material, for example of titanium or titanium alloy.

The present invention also has as its object a very specific use of the distractor answering the aforementioned characteristics, for a distraction in a near continuous mode, wherein this use is remarkable by the fact that the rotation of the integral pin of the worm screw is controlled so as to compress again the resilient part as soon as the end of the worm screw that is not resting against said resilient part comes again into contact with the inner wall of the bearing that faces said end.

These various essential specifications make obvious for the one skilled in the art the additional advantages afforded by the intraoral jaw distractor according to the invention relative to the prior art.

The detailed specifications of the invention are given in the following description in relation to the attached drawings. It must be noted that these drawings have no other purpose than to illustrate the text of the description and that they thus do not constitute in any way a limitation of the scope of the invention.

DESCRIPTION OF THE PREFERRED EMBODIMENTS OF THE INVENTION

Figure 1:
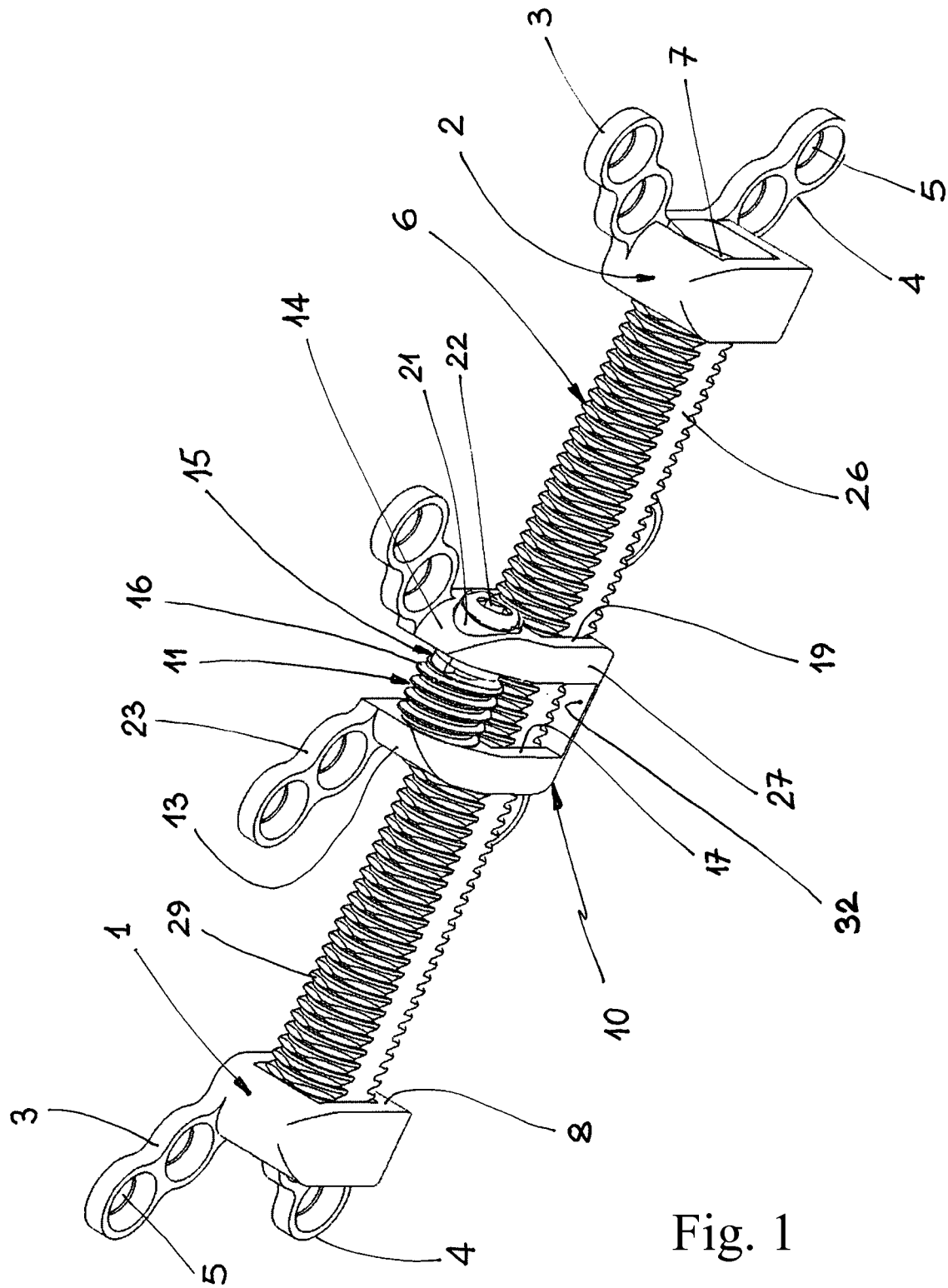
FIG. 1 is a perspective view of the front of a customized intraoral jaw distractor according to the invention, executed in its first embodiment in which the threaded cylindrical rail is rectilinear.

The customized intraoral jaw distractor executed according to the invention includes in known manner two anchoring means, respectively left 1 and right 2, fastened in the patient's mandibular body at anchor points determined by the operator and located on each side of the osseous callus.

In order to constitute fixed anchor points, each of these two anchoring means 1 and 2 preferably comprise two lugs 3 and 4 forming together for example an angle on the order of 90 to 120°, wherein each lug is for example provided with two openings 5 through which will pass screws or spindles (not represented) that will thus ensure said anchoring means are fastened in the immobile osseous segments of the mandibular body.

A threaded cylindrical rail 6, connecting the two anchoring means 1 and 2, constitutes the basis of the distractor according to the invention, in the sense that it will allow the bone trajectory of the reconstruction to be defined very accurately.

To this effect, each of the two ends of the rail 6 comes to lodge in a recess 7 provided in the inner wall 8 of each of the two anchoring means 1, 2 opposite the lugs 3, 4.

Each end of the rail 6 is then fastened in said recess 7 into which it penetrates, with the aid of a screw 9 passing through a threaded hole bored between the top (or the base or also of a longitudinal wall) and the housing 7 of each of the anchoring means 1, 2.

A carriage 10, mobile, capable of sliding on the rail 6, and guided by the latter, is fastened onto the osseous segment to be distracted.

In order to enable it to slide, the mobile carriage 10 is provided with a worm screw 11 whose thread that complements that of the rail 6 and engages with the latter. The pitch of the worm screw/rail thread unit is chosen to correspond with the displacement values classically used for the distraction.

The worm screw 11 is bored with a through-hole extending along the longitudinal axis of said screw, in which through-hole is lodged a central pin 12 that overshoots on each side of the worm screw 11 and whose role is to control the rotation of said screw. The pin 12 is made integral to the worm screw 11, either by being tightly mounted or by welding or by gluing, for example by means of a cyanoacrylate glue.

The pin 12 thus integral to the worm screw 11 is therefore roughly parallel to the stationary rail 6 and is supported by two bearings, left 13 and respectively right 14, arranged on the mobile carriage 10 on either side of the worm screw.

Finally, at least one resilient part 15 traversed by the pin 12 rests on the one hand against one end 16 of the worm screw 11 and on the other hand against the inner wall 18 of the bearing 14 that faces said end 16, wherein the distance separating the inner walls 17 resp. 18 of the two bearings 13 and 14 of the mobile carriage 10 is equal to the length of the worm screw 11 increased by the height of the resilient part 15 when the latter is resting, i.e. is slack.

The central pin 12 overshoots on each side of the worm screw 11 so as to be supported by the bearings 13 and 14 respectively in a housing bored in the inner wall 17 of the bearing 13 and in a guide bored in the inner wall 18 of the bearing 14, said guide going through said bearing 14 and emerging in its outer wall 19.

A recess 20 of a diameter greater than that of the guide is made in said outer wall 19 and, in complementary fashion, the end of the central pin 12 of the worm screw 11 is provided with a head 21 that can be accommodated in the recess 20.

From all the preceding, it will be understood that the central pin 12 is made integral to the worm screw 11 after said screw and the resilient part 15 have been put in place side by side between the two bearings 13 and 14, against their inner sides, respectively 17 and 18, and after said pin has been mounted through the guide of the bearing 14, the resilient part 15 and then the longitudinal hole of the worm screw 11, and finally accommodated in the bearing 13.

The two ends of the central pin 12 can turn freely in the bearings 13 and 14 that support said central pin.

Due to its construction, the depth of the housing bored in the inner wall 17 of the bearing 13 is at least equal to the length of the part of the central pin 12 that overshoots from the worm screw 11 and which is intended to penetrate into said housing, and the length of this protruding part of the central pin 12 is greater than the maximum thickness loss that the resilient part can encounter during its compression.

Figure 5:
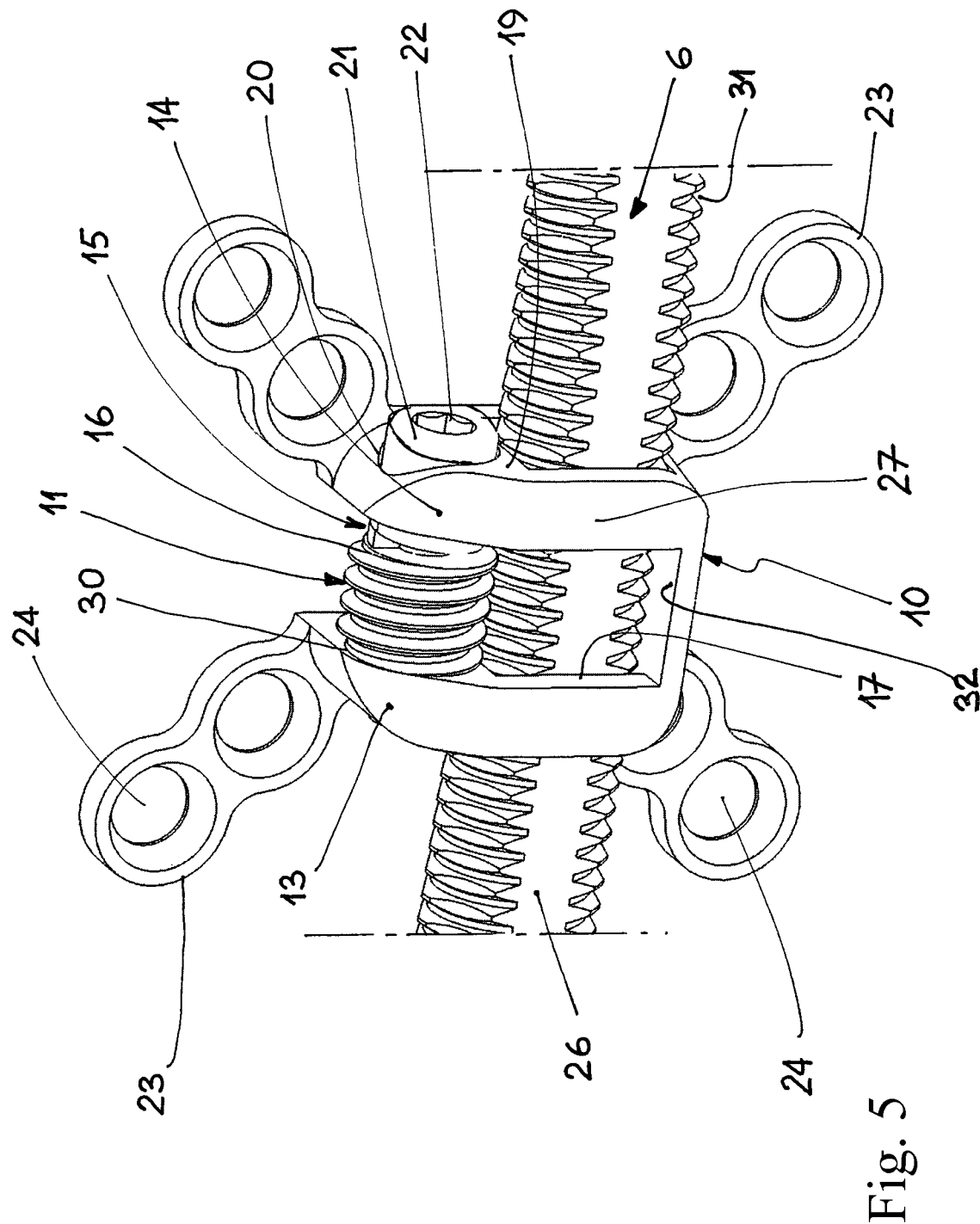
FIG. 5 is a perspective view of the mobile carriage represented in FIG. 4.
Figure 6:
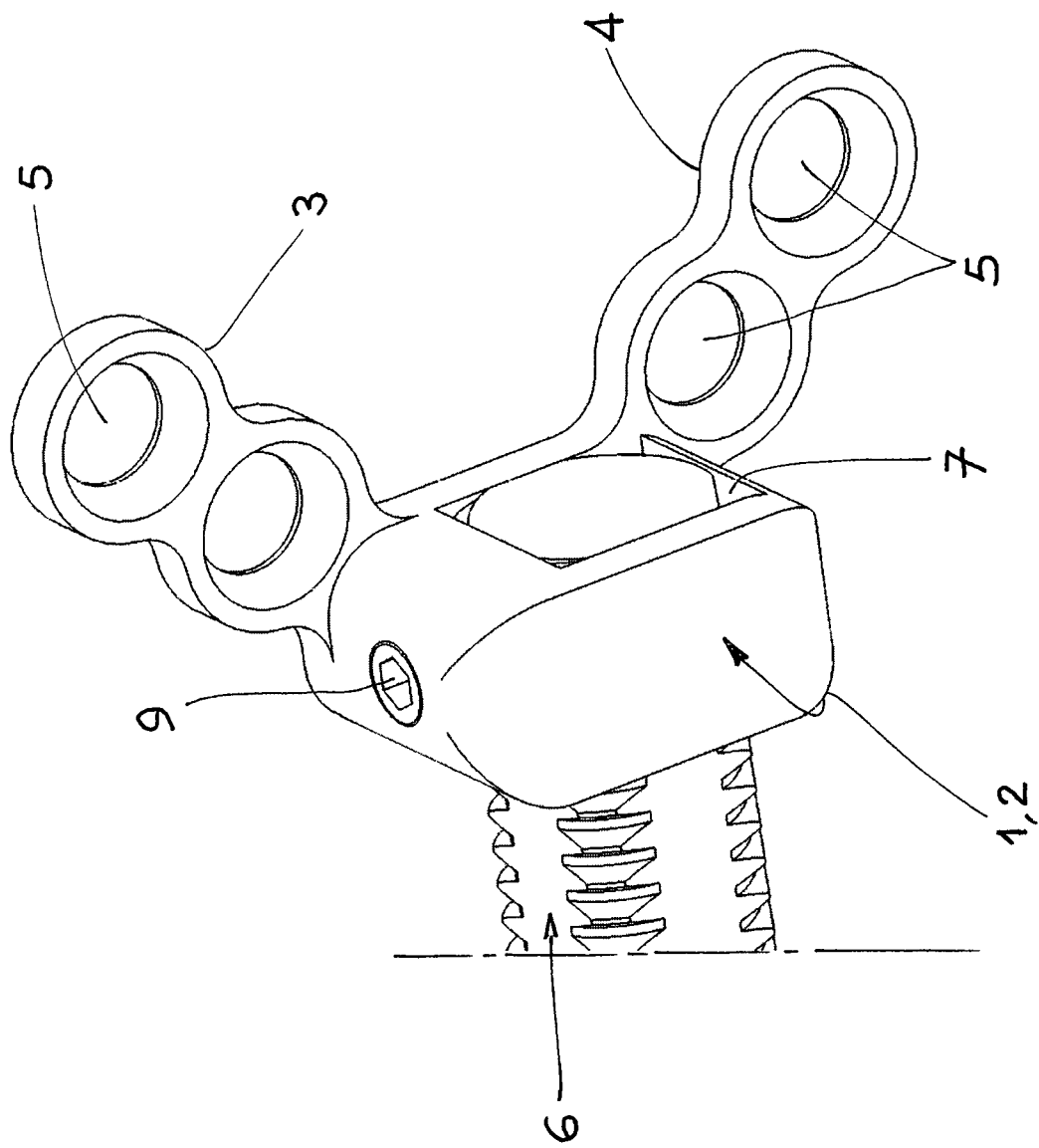
FIG. 6 is a perspective view of one of the two fixed anchoring means of the distractor according to the invention, said anchoring means being capable of being fastened in the mandibular body on either side of the osseous callus.

The head 21 of the central pin 12 is further provided with means 22 enabling it to be rotated, for example in the form of a slit or two slits arranged in a cross, capable of engaging with a screwdriver, or in the form of a six-sided blind hole, as represented in FIG. 5, capable of engaging with an Allen wrench.

As the central pin 12 and the worm screw 11 have been made integral to one another, it is clear that the rotation operation of the head 21 of the pin 12 by means of a screwdriver or an Allen wrench controls the rotation of the worm screw 11 as a whole.

The resilient part 15 with which the mobile carriage 10 is fitted is chosen to behave in the axial direction as a spring with low space requirements and relative rigidity. Thus, the force necessary for compressing this resilient part is therefore chosen to be slightly lower than that required for moving the osseous segment to be distracted away from the immobile osseous segment from which it originates after fracture.

The resilient part 15 can thus be an elastic washer, for example either a conical washer also called Belleville conical spring washer, or a stack of such conical washers arranged in opposition to one another, or preferably a lock-type washer, i.e. a ring washer which is split and which, in the area of that split, is considerably deformed axially.

It is thus a lock-type washer that has been represented by way of example in all the drawings attached to the present description. However, the resilient part 15 can also be made in a shape technically equivalent to a washer, for example a spring, a diaphragm or a compressible cylinder, for example made of elastomer.

Finally, the mobile carriage 10 is provided with fastening means in the osseous segment to be distracted. These means are for example wings 23 overextending on each side of said carriage and integral to it, and having for example the shape of an I, of a Y or of a crossbuck as represented in FIGS. 1 to 5.

Each wing 23 of the crossbuck is then advantageously bored with two holes 24 through which will pass screws or spindles (not represented) that will ensure the mobile carriage 10 is fastened into the osseous segment to be distracted.

From all that precedes, it will be understood that by controlling the rotation of the worm screw 11 by means of a screwdriver or an Allen wrench actuating the head 21 of the central pin 12 integral to said worm screw, it is possible to compress the resilient washer 15 without displacing the carriage 10 or at least by moving it only imperceptibly, thus without this operation moving the osseous segment to be distracted away from the immobile osseous segment.

In the example represented, if this rotation operation is performed anticlockwise, the resilient washer 15 will be progressively compressed, the worm screw 11 then pressing with its end 16 on said resilient washer whilst simultaneously the other end 30 of the worm screw moves away from the inner wall 17 of the bearing 13.

During this deformation, the resilient washer will accumulate a certain quantity of energy, equal to the effort exerted by the force that enabled it to be compressed, and store it in the form of potential elastic energy.

In practice, during the aforementioned rotation of the worm screw, the washer 15 is compressed in the manner of a spring but the osseous segment to be distracted does not move, or moves only imperceptibly. During the hours that follow, the potential elastic energy stored by the washer 15 is released, which has the effect that the washer then tends to slowly resume its initial resting shape, i.e. to become slack, until said potential elastic energy falls to zero. In other words, the washer 15 relaxes by resting on the extremity 16 of the worm screw, which is immobilized, and it thus pushes back the bearing 14; the carriage 10 will then be displaced very progressively by the same movement, from the left to the right as indicated by the arrow 25 in FIG. 4, always driving in the same progressive movement the osseous segment to be distracted. The distraction thus occurs in a near continuous manner, by contrast to what the distractors known so far can afford. Yet, according to the most recent research, it seems that osteogenesis performance would be all the more enhanced if the distraction were performed in a manner as continuous as possible. The distractor according to the invention thus allows the success rate of the treatment to be improved whilst reducing the time required therefor.

In order to achieve a distraction in a continuous or near continuous mode, the practitioner (or the patients themselves) will ensure that, as soon as the end 30 of the worm screw 11 that is not resting against the resilient washer 15 will come (or return) into contact with the inner wall 17 of the bearing 13 that faces said end 30, the previous operation is repeated during which, by actuating the head 21 of the central pin 12 of said worm screw, the resilient washer 15 had been compressed. Since there will thus be continuity in the distraction process, the practitioner will in practice be able to act daily, or even twice daily, by compressing each time the washer 15, thus reducing its thickness by several tenths of a millimeter up to two millimeters, and increasing by the same distance, but this time progressively, the osseous segment to be distracted relative to the immobile osseous segment.

The mobile carriage 10 of the distractor according to the invention will have to be guided perfectly by the rail 6 as long as the distraction will require it.

To this effect, the standard threaded rod from which the rail 6 will be made will be subjected to a particular machining process consisting in providing, on the entire length of said rod, two diametrically opposed flat faces 26, roughly parallel to the lugs 3 of the anchoring means 1 and 2.

According to a preferential complementary construction, the mobile carriage 10 will then have the shape of a cage whose two lateral walls, front 27 and respectively rear 28, parallel to the longitudinal axis of the rail 6 and to the latter's flat faces 26, will be joined at their two ends by one and the other of the two bearings 13 and 14, said two walls 27 and 29 being further spaced by a distance very slightly greater than the thickness of said rail 6 taken between its two flat faces.

In a first embodiment, the most common one, the rail 6 will be rectilinear, as has been represented in FIG. 1.

However, providing the two flat faces 26 will enable other infinitely more complex embodiments to be achieved, in which the rail 6 will form one or several curves, thus imposing the ideal displacement sought by the practitioner to the osseous segment to be distracted.

Figure 2:
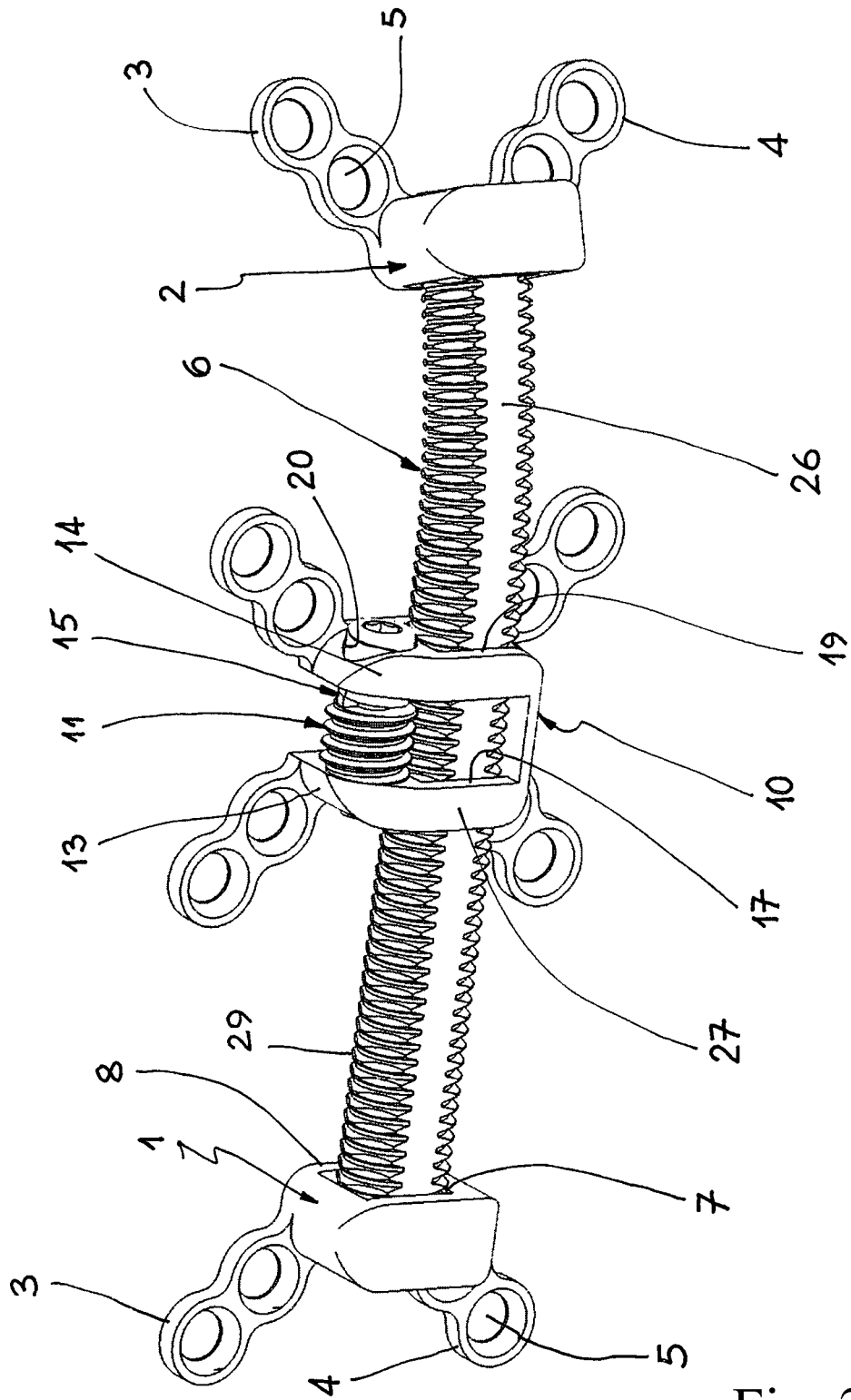
FIG. 2 is a perspective view of the front of a customized intraoral jaw distractor according to the invention, executed in its second embodiment in which the threaded cylindrical rail is curved.
Figure 3:
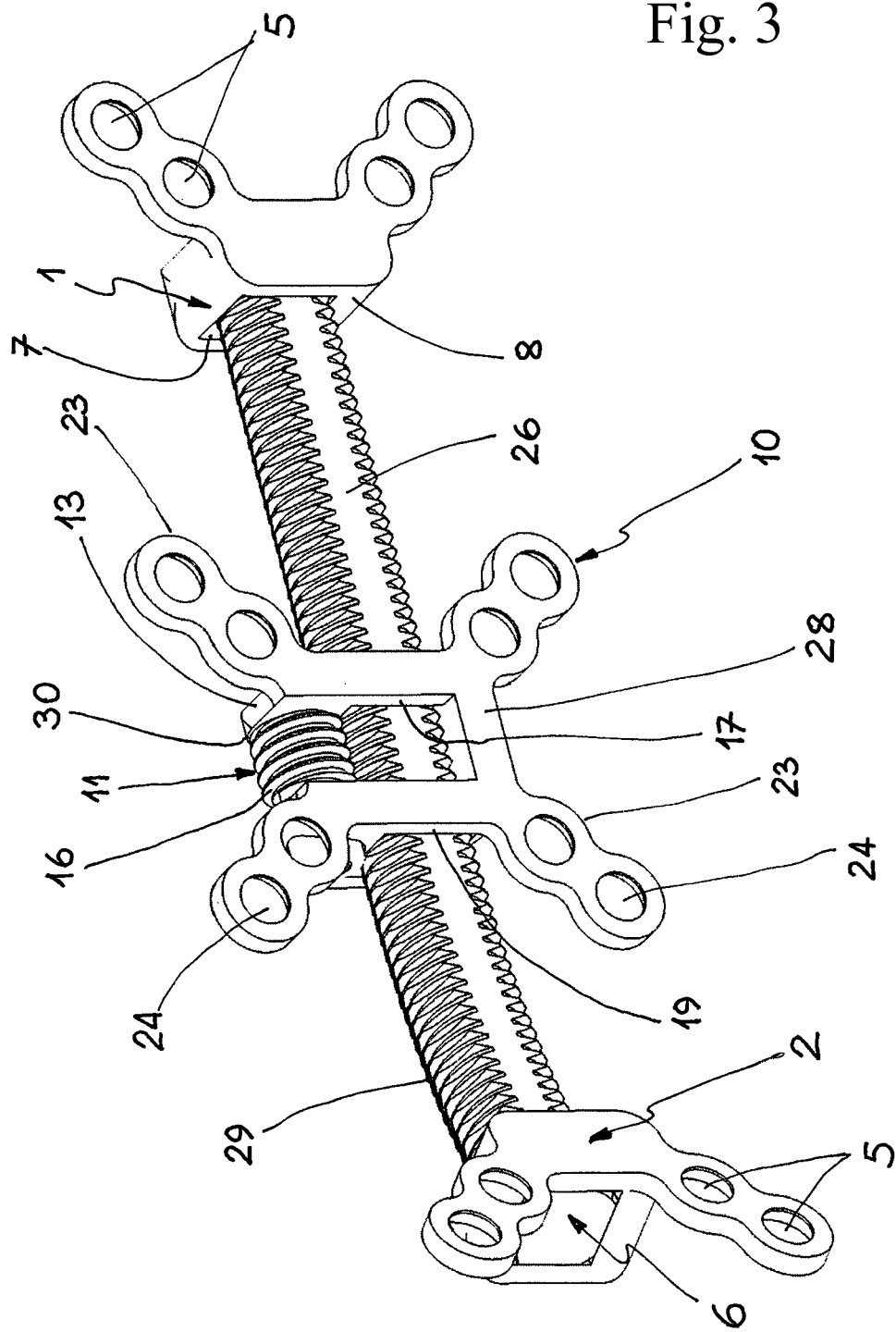
FIG. 3 is a perspective view of the rear of the distractor of FIG. 2.
Figure 4:
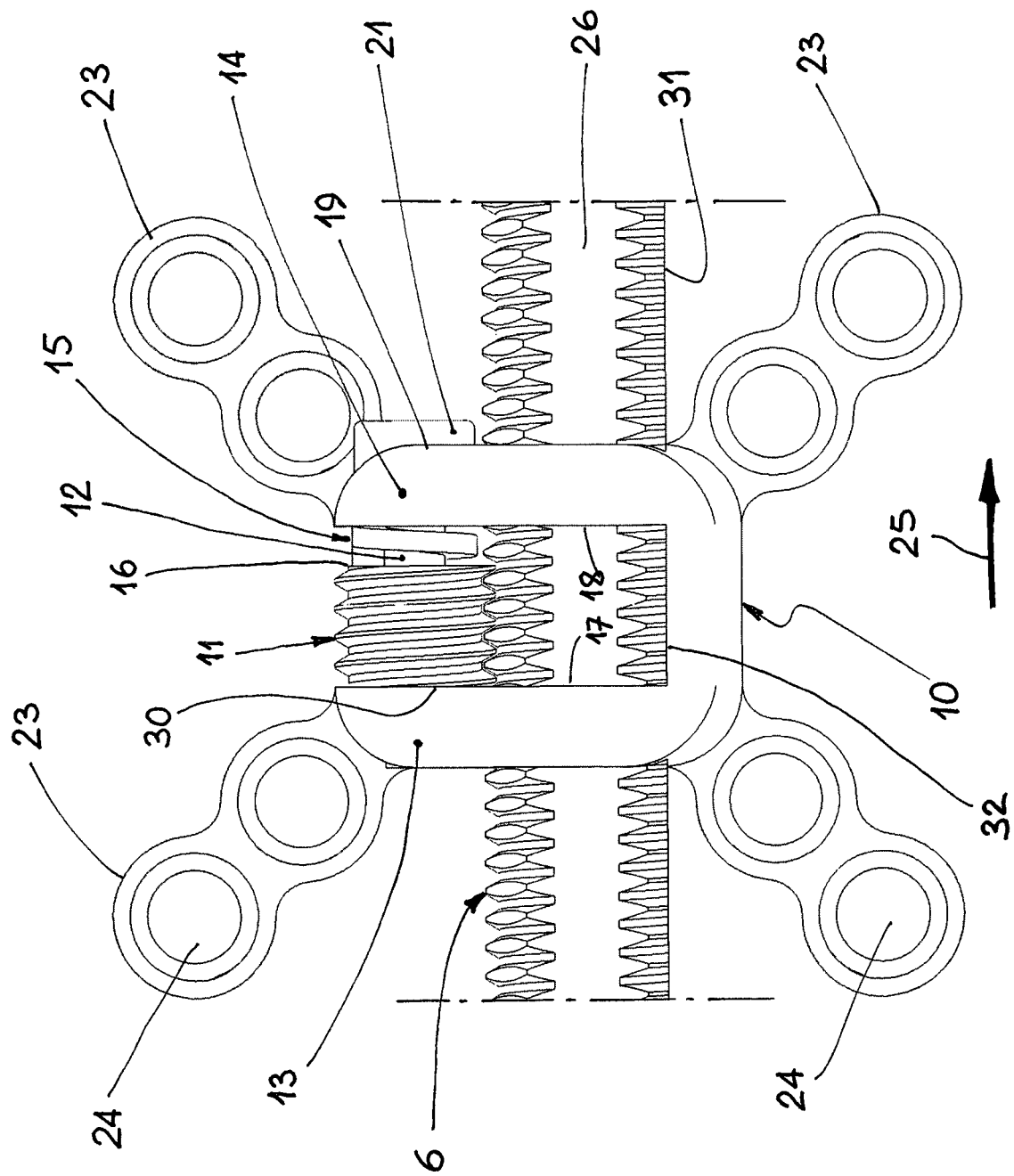
FIG. 4 represents, in a frontal view from the front, a more detailed view of the mobile carriage guided to slide on the threaded cylindrical rail.

One example of a single-curve rail has been represented in FIGS. 2 and 3.

It is however conceivable that the rail can be curved in a customized manner and include several curves, overall with the same concavities or inverted concavities, and that it thus follows as closely as possible the inside shape of the patient's jaw, the only limitation of these various curves being that they lie within a single plane, which can be identified in that it is perpendicular to the rail's flat faces 26, this being so as to maintain the original threading of the rod in the vicinity of the neutral fibers 29 of said rail that are not subjected to any extension nor compression when the curves are made. The nominal features of the screw head profile and of the pitch of the threaded rod will thus be maintained and the rail's threading will engage perfectly with the worm screw without being affected at all, whatever the quantity and shape of the curves of said rail.

The distractor according to the invention can thus be specific to each patient and be made in a customized manner from data obtained using computers preoperatively.

Another advantage of such a distractor is its great compactness. Its overall thickness, including the fittings, is indeed 6 millimeters. This particularity is obviously of prime importance when simultaneously considering the intraoral character of this device.

Still by reason of its intraoral character, each of the constitutive elements of the distractor according to the invention, including each of its fastening screws, will be made of a biocompatible material, for example of titanium or titanium alloy.

According to yet another embodiment, and with the aim of further improving the stability of the mechanism, it is easy to conceive a distractor corresponding to the one described further above and wherein the threaded rail 6 has a third flat face extending over the entire length of the lower part 31 of the rail, i.e. opposite the bottom 32 of the cage constituting the mobile carriage 10. The mobile carriage 10 will thus be guided even better along the rail 6 since three of its inner sides, those present on its two lateral walls respectively front 27 and rear 28 and that present on its bottom 32, will be in the immediate vicinity of the three flat faces 26 and 31 provided on the rail 6. In this embodiment, with the exception of the attachment zones between the flat faces, it is then essentially the upper part of the rail that will show the threading indispensable for operating the worm screw 11 and, consequently, indispensable for moving the carriage 10.

Of course, the invention is not limited to the only preferred embodiments described here above.

On the contrary, it includes all possible variant embodiments inasmuch as they remain within the frame defined by the following claims.

The invention claimed is:

1. A customized intraoral jaw distractor comprising:
a) a threaded cylindrical rail connecting two anchoring means configured to attach to a mandibular body at anchor points, located on both sides of an osseous segment,
b) a mobile carriage guided to slide on the threaded cylindrical rail and configured to attach to the osseous segment to be distracted, said mobile carriage being provided with a worm screw with a thread that complements a thread on the rail and engages with the threaded cylindrical rail on the threaded cylindrical rail,
c) a pin integral to the worm screw, the pin configured to control the rotation of the worm screw, said pin, which is roughly parallel to the threaded cylindrical rail, being supported by first and second bearings arranged on the mobile carriage, wherein the first bearing on the mobile carriage is adjacent to a first section of the worm screw and wherein the second bearing is in contact with a second section of the worm screw; and
d) at least one resilient part through which said pin passes and which rests on a first side against one end of the worm screw and on a second side against a first inner wall of the first bearing that faces said end, wherein a distance separating the first inner wall of the first bearing and a second inner wall of the second bearing is equal to a length of the worm screw increased by a height of the at least one resilient when the resilient part is resting, wherein the at least one resilient part has a resting shape that is compressed through a rotation of the worm screw, and
wherein, subsequent to the rotation of the worm screw, the at least one resilient part resumes the resting shape resulting in a continuous or near-continuous movement of the mobile carriage.

2. The intraoral jaw distractor of claim 1, wherein the at least one resilient part is comprised of one or more lock-type resilient washers.

3. The intraoral jaw distractor of claim 1, wherein the at least one resilient part is a spring.

4. The intraoral jaw distractor of claim 1, wherein the pin controlling the rotation of the worm screw is provided with an actuator head lodged in a recess made in an outer wall of the first bearing against which the at least one resilient part rests.

5. The intraoral jaw distractor of claim 4, wherein the actuator head provided on the pin controlling the rotation of the worm screw has a slit, or two slits arranged in a cross, or a six-sided blind hole enabling said head to rotate by means of a screwdriver or an Allen wrench.

6. The intraoral jaw distractor of claim 1, wherein the two anchoring means and the mobile carriage comprise lugs and wings respectively, the lugs and wings provided with two openings through which will pass screws or spindles that will thus ensure they are attached in the mandibular body and respectively in the osseous segment to be distracted.

7. The intraoral jaw distractor claim 6, wherein the wings are in the shape of an I, of a Y or of a crossbuck.

8. The intraoral jaw distractor of claim 1, wherein the threaded cylindrical rail has two diametrically opposed flat faces, wherein the mobile carriage guided to slide on said rail has the form of a cage having two walls, the first and second parallel to a longitudinal axis of the threaded cylindrical rail and joined by bearings supporting the pin of the worm screw, are spaced by a distance greater than the thickness of said threaded cylindrical rail taken between its two flat faces.

9. The intraoral jaw distractor of claim 8, wherein the threaded cylindrical rail has a third flat face opposite a bottom surface of the mobile carriage.

10. The intraoral jaw distractor of claim 9, wherein the threaded cylindrical rail is rectilinear.

11. The intraoral jaw distractor of claim 9, wherein the threaded cylindrical rail forms at least one curve.

12. The intraoral jaw distractor of claim 11, wherein the at least one curve of the threaded cylindrical rail lies in a single plane.

13. The intraoral jaw distractor of claim 1, wherein each of the constitutive elements is made of a biocompatible material.

14. The intraoral jaw distractor of claim 1, wherein the at least one resilient part is comprised of one or more Belleville conical spring washers.

15. The intraoral jaw distractor of claim 1, wherein the at least one resilient part is a diaphragm.

16. The intraoral jaw distractor of claim 1, wherein the at least one resilient part is a compressible cylinder.

17. The intraoral jaw distractor of claim 1, wherein the at least one resilient part is made of elastomer.

18. The intraoral jaw distractor of claim 1, wherein each of the constitutive elements is made of titanium.

19. The intraoral jaw distractor of claim 1, wherein each of the constitutive elements is made of titanium alloy.

20. The use of the intraoral jaw distractor of claim 1 for a distraction in a near continuous mode, wherein the rotation of the integral pin of the worm screw is controlled so as to compress against the at least one resilient part as soon as the end of the worm screw that is not resting against said resilient part comes again into contact with the first inner wall of the bearing that faces said end.

* * * * *